United States Patent

Nakazeki et al.

[11] Patent Number: 5,911,558
[45] Date of Patent: Jun. 15, 1999

[54] MAGNETICALLY SUSPENDED PUMP HAVING POSITION SENSING CONTROL

[75] Inventors: Tsugito Nakazeki; Minoru Suzuki, both of Shizuoka; Toshihiko Nojiri, Kanagawa, all of Japan

[73] Assignee: NTN Corporation, Osaka, Japan

[21] Appl. No.: 08/848,408

[22] Filed: May 8, 1997

[30] Foreign Application Priority Data

May 10, 1996 [JP] Japan ................... 8-116075

[51] Int. Cl.⁶ .................................................... F01B 25/26
[52] U.S. Cl. .......................................... 415/118; 415/900
[58] Field of Search .................................. 415/118, 900; 417/63, 423.7, 428.12; 310/90.5

[56] References Cited

U.S. PATENT DOCUMENTS

| | | | |
|---|---|---|---|
| 5,112,202 | 5/1992 | Oshima et al. | 417/423.7 |
| 5,350,283 | 9/1994 | Nakazeki et al. | 417/423.7 |
| 5,686,772 | 11/1997 | Delamare et al. | 310/90.5 |
| 5,725,357 | 3/1998 | Nakazeki et al. | 415/900 |

Primary Examiner—Christopher Verdier
Assistant Examiner—Ninh Nguyen
Attorney, Agent, or Firm—McDermott, Will & Emery

[57] ABSTRACT

Permanent magnets are buried on one side of an impeller, and a rotor having permanent magnets buried opposite thereto is provided to form a passive bearing. On the other side of the impeller, three electromagnet coils and three position sensors are circumferentially provided at equal distances to form an active bearing, the outputs of the three position sensors are operated to produce impeller displacements, which are fed back to drive the coils.

4 Claims, 5 Drawing Sheets

$$Z = (S1 + S2 + S3) / 3$$

$$\theta y = (S1 - S2) / \sqrt{3}r$$

$$\theta x = (S1 + S2 - 2S3) / 3r$$

$Z = (S1 + S2 + S3) / 3$ $\theta y = (S1 - S2) / \sqrt{3} r$ $\theta x = (S1 + S2 - 2S3) / 3r$ $$Z = (S1 + S2 + S3)/3$$
$$S1' = Z + (Z - S3)$$
$$= (2S1 + 2S2 - S3)/3$$
$$S2' = (-S1 + 2S2 + 2S3)/3 \quad (1)$$
$$S3' = (2S1 - S2 + 2S3)/3$$

$Z = (S1+S2+S3+S4)/4$ $\theta x = ((S1+S2) - (S3+S4))/2\sqrt{2}r$ $\theta y = ((S1+S4) - (S2+S3))/2\sqrt{2}r$

MAGNETICALLY SUSPENDED PUMP HAVING POSITION SENSING CONTROL

BACKGROUND OF THE INVENTION

1. Field of the Invention

The present invention relates generally to magnetic pumps, and more particularly, to a magnetically suspended pump for use in medical equipment such as artificial heart-lung machine and artificial heart. The magnetically suspended pump supports an impeller by a magnetic bearing and rotates the impeller by a motor through a partition by means of magnetic coupling.

2. Description of the Background Art

FIGS. 4A and 4B are views showing a conventional magnetically suspended blood pump. In FIG. 4A, an impeller 3 is provided in the casing 2 of a magnetically suspended blood pump 1. Casing 2 formed of a nonmagnetic material includes a nonmagnetic member 5 having permanent magnets 4 which forms a passive magnetic bearing and a soft iron member 6 which corresponds to the rotor of an active magnetic bearing. Permanent magnets 4 are divided along the circumference of impeller 3, and adjacent magnets are polarized in the opposite directions to one another.

On the side opposite to the side with the permanent magnets 4 of impeller 3, a rotor 7 is provided separated from impeller 3 by casing 2. Rotor 7 is driven to rotate by a motor 9. Rotor 7 is provided with permanent magnets 8 of the same number as and opposite to the permanent magnets 4 of impeller 3 such that the attracting force is effected between them.

Meanwhile, electromagnets 10 and position sensors S1 to S4 are provided opposite to the side of the soft iron member 6 of impeller to retain impeller 3 in the center of casing 2 against the attracting force between permanent magnets 4 and 8. Position sensors S1 to S4 are provided between the coils M1 to M4 of electromagnets 10 as shown in FIG. 4B.

In magnetically suspended blood pump 1 having the above-described structure, permanent magnets 8 incorporated in rotor 7 drive and radially support impeller 3, and cause the axial attracting force between permanent magnets 4 provided to impeller 3 and them. Current corresponding to the attracting force is passed through the coils of electromagnets 10, which causes impeller 3 to be suspended. Then, rotor 7 is rotated by the driving force of motor 9 to generate magnetic coupling between permanent magnets 4 and 8, which rotates impeller 3, and blood is introduced from an inlet port to an outlet port which are not shown. Impeller 3 which is separated from rotor 7 by casing 2 is not contaminated by electromagnets 10, and therefore blood discharged from magnetically suspended blood pump 1 maintains its clean state. FIG. 5 is a diagram showing a control circuit for the magnetically suspended blood pump as shown in FIGS. 4A and 4B. The Z-axis, $\theta_x$-axis and $\theta_y$-axis are produced by operations according to the following expressions using an operation circuit (not shown) based on signals from position sensors S1 to S4 shown in FIG. 4.

$$Z = (S1 + S2 + S3 + S4)/4$$
$$\theta_x = ((S1 + S2) - (S3 + S4))/2\sqrt{2}r$$
$$\theta_y = ((S1 + S4) - (S2 + S3))/2\sqrt{2}r$$

wherein r is the radius of electromagnet 10.

The values of Z, $\theta_x$ and $\theta_y$ produced as above are input to PID (Proportional integral Derivative) compensators 11 to 13 shown in FIG. 5, the output of PID compensator 11 is applied to one input end of each of adders 16 to 19. The output of PID compensator 12 is applied to the other input end of adder 16, also added with a coefficient by a coefficient unit 14 and applied to the other input end of adder 18. The output of PID compensator 13 is applied to the other input end of adder 19, also added with a coefficient by a coefficient unit 15 and applied to the other input end of adder 17. Adders 16 to 19 add the respective two inputs, and apply the results to amplifiers 20 to 23. Amplifiers 20 to 23 drive corresponding coils M1 to M4.

The magnetically suspended blood pump 1 shown in FIGS. 4A and 4B requires the four coils M1 to M4 and four position sensors S1 to S4 for electromagnets 10 which constitute the active magnetic bearing. Although reducing the number of such coils and position sensors for electromagnets 10 naturally reduces manhour involved and improves the reliability, but on the other hand if the number of coils and sensors are reduced to three, the circumference of each magnet will be longer, and $\theta_x$ and $\theta_y$ cannot be accurately controlled.

SUMMARY OF THE INVENTION

It is therefore a main object of the invention to provide a magnetically suspended pump with a reduced number of elements such as coils and sensors to constitute a magnetic bearing, thereby reducing the cost, and improving the reliability.

Briefly stated, according to the invention, two radial axes of a disk shaped impeller are passively controlled by a passive magnetic bearing, and two axes around the center of gravity and the axial direction of the impeller are actively controlled by an active bearing. The active bearing includes three position sensors and three electromagnets circumferentially provided at equal distances opposite to the impeller, an operation is conducted based on a prescribed operation expression according to the output signals of the three position sensors to generate a feedback signal for each electromagnet and a corresponding electromagnet is controlled.

Therefore, according to the present invention, the number of elements to form position sensors and electromagnets may be reduced to reduce necessary manhour, the impeller may be formed compact and magnetically suspended in a stable manner, thereby improving the reliability. Such a compact device may be readily installed into a body when used as a blood pump.

In a preferred embodiment, the following operation expressions are used, wherein the axial component is Z, the output signals of the three position sensors are S1, S2 and S3, and the impeller displacements of the three electromagnets are S1', S2' and S3':

Z=(S1+S2+S3)/3
S1'=Z+(Z−S3)=(2S1+2S2−S3)/3
S2'=(−S1+2S2+2S3)/3
S3'=(2S1−S2+2S3)/3

More preferably, a passive bearing includes a first permanent magnet provided on one side of an impeller, and a rotor having a second permanent magnet provided opposite to that one side of the impeller and opposing the first permanent magnet, and the rotor is driven to rotate by a motor. On the other side of the impeller, a soft iron member is provided opposite to the electromagnet.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

Figure 1:
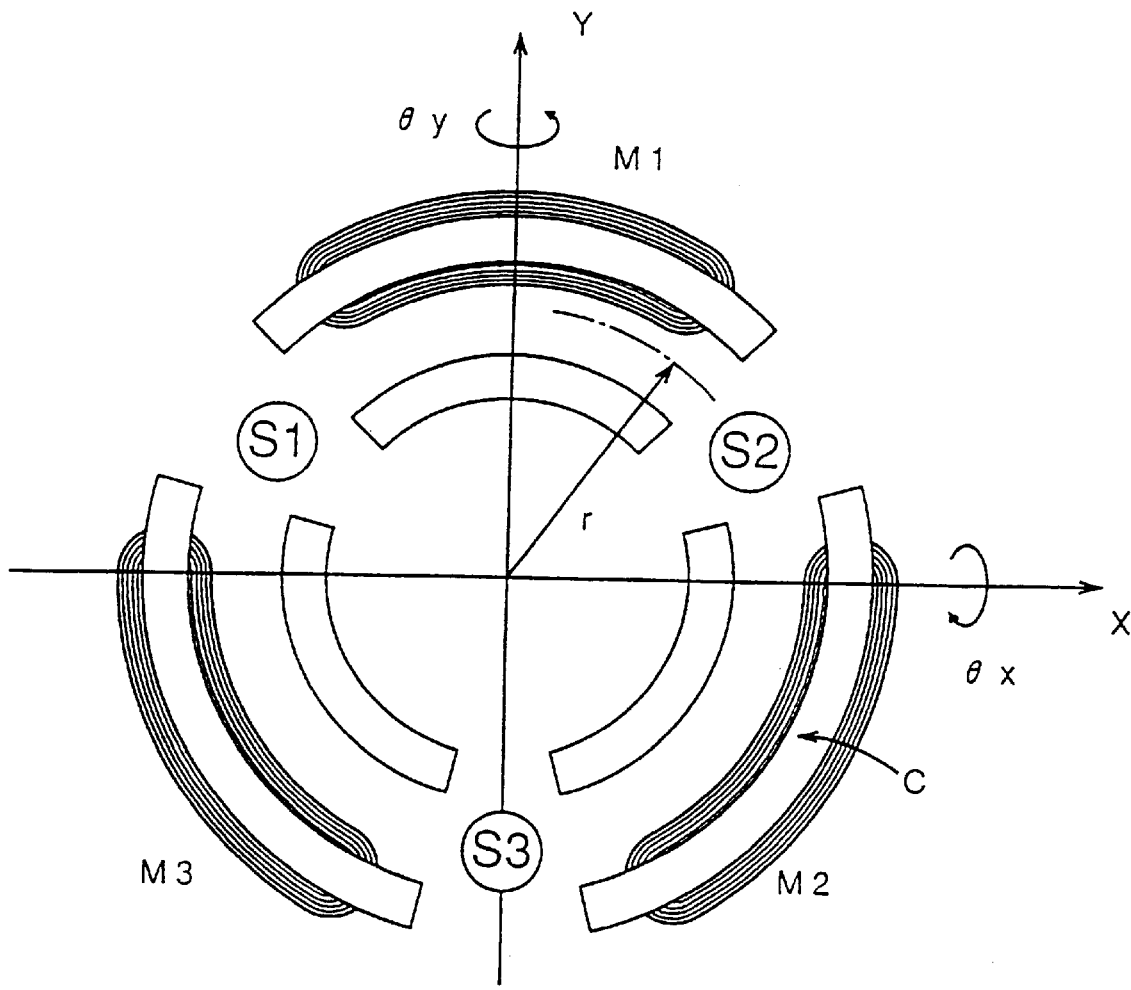
FIG. 1 is a view showing the arrangement of electromagnets and position sensors according to an embodiment of the invention.
Figure 4A:
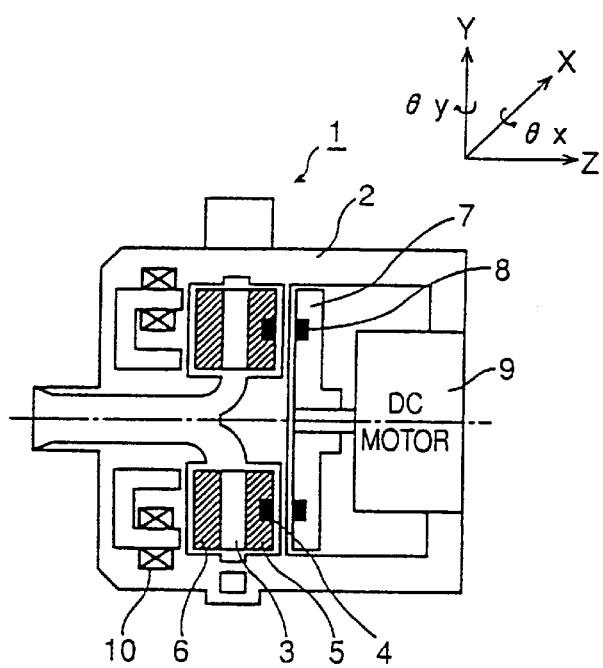
FIGS. 4A and 4B are views showing a conventional magnetically suspended blood pump.
Figure 4B:
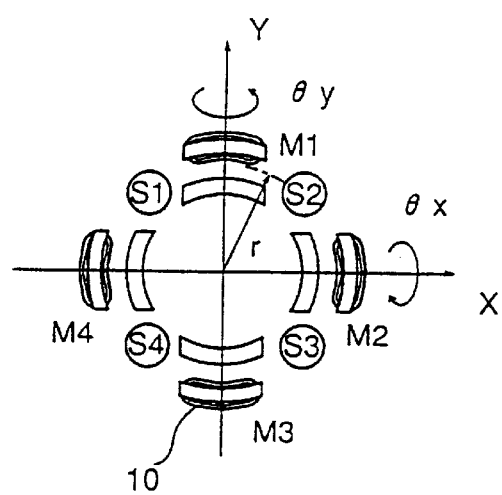
Figure 5:
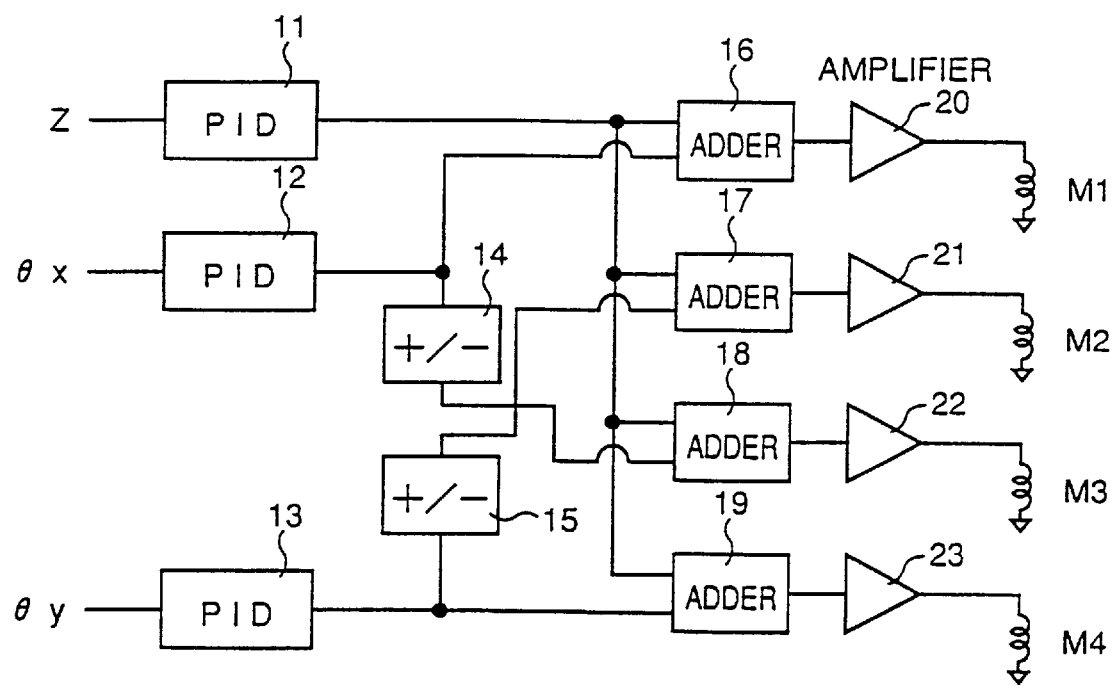
FIG. 5 is a diagram showing a control circuit for the magnetically suspended blood pump shown in FIGS. 4A and 4B.

FIG. 1 is a diagram showing an embodiment of the invention, which is to be compared to FIG. 4B showing conventional position sensors and electromagnet coils. In FIG. 1, according to the embodiment, three coils M1 to M3 are provided as electromagnets, and position sensors S1 to S3 are provided between coils M1 to M3. The other structure is the same as that shown in FIG. 4A.

The Z-axis, $\theta_x$-axis and $\theta_y$-axis are represented as follows:

$$Z = (S1 + S2 + S3)/3$$
$$\theta_x = (S1 + S2 - 2S3)/3r$$
$$\theta_y = (S1 - S2)/\sqrt{3r}$$

However, use of these expressions makes it difficult to accurately control $\theta_x$ and $\theta_y$, because the circumference of each electromagnet is long.

Therefore, according to the embodiment, the displacements S1' to S3' of the impeller for points C in the center of the electromagnets are produced by operating signals from position sensors S1 to S3.

Figure 2:
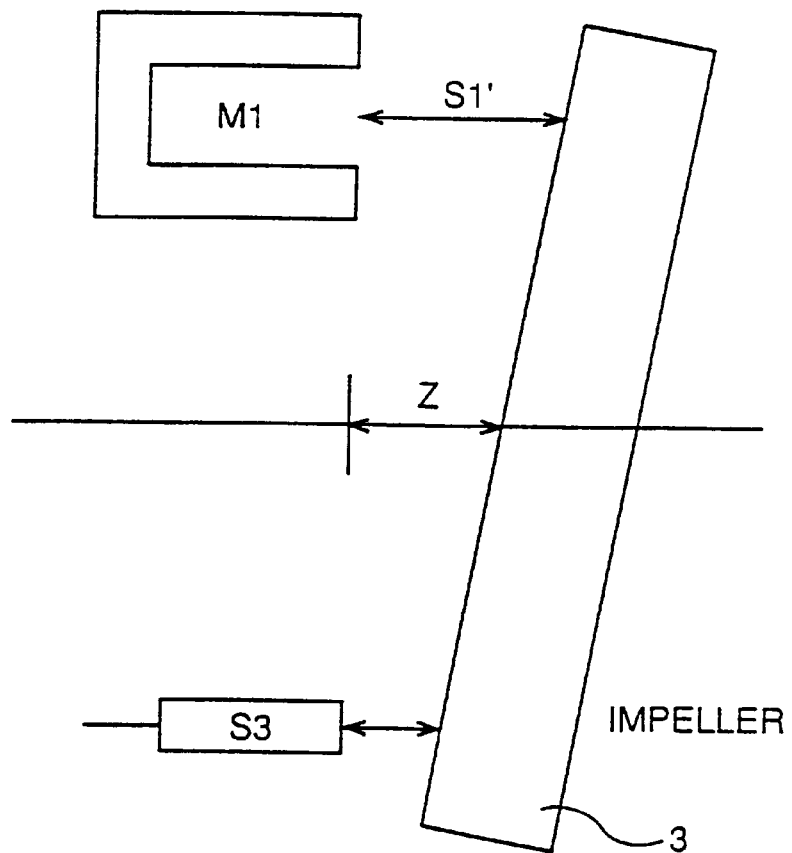
FIG. 2 is a diagram for use in illustration of a method of producing a displacement of point C of each electromagnet.

FIG. 2 is a diagram for use in illustration of a method of producing a displacement of point C of each electromagnet. In FIG. 2, impeller displacement S1' for coil M1 is produced, and the same method may be applied to the electromagnets of coils M2 and M3 to produce the displacements of impeller 3 around the magnets according to the following expressions:

Z=(S1+S2+S3)/3
S1'=Z+(Z-S3)=(2S1+2S2-S3)/3
S2'=(-S1+2S2+2S3)/3
S3'=(2S1-S2+2S3)/3

Figure 3:
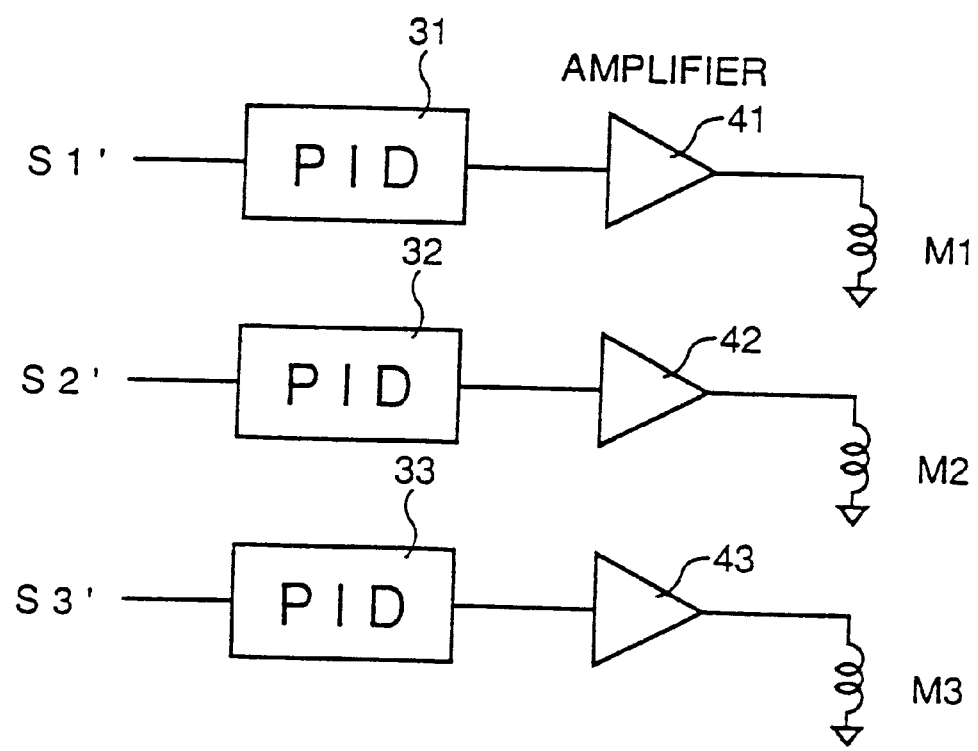
FIG. 3 is a block diagram showing a driving circuit for driving the electromagnets shown in FIG. 1.

FIG. 3 is a block diagram showing a driving circuit for driving coils M1 to M3 shown in FIG. 1. The displacement signals S1', S2' and S3' of the impeller produced based on the above expressions are input to amplifiers 41 to 43 through PID compensators 31 to 33, and coils M1 to M3 are driven as a result.

Thus, the impeller displacements S1' to S3' of coils M1 to M3 are produced, the displacements are fed back to control coils M1 to M3, and therefore the $\theta_x$-axis and $\theta_y$-axis may be accurately controlled, so that the impeller may be magnetically suspended in a stable manner. In addition, since the number of elements for the electromagnets and position sensors is reduced, the involved manhour may be reduced accordingly, and therefore the device may be formed compact with an improved reliability. Furthermore, if the magnetically suspended pump is used as a blood pump, the compact structure is advantageously suitable for installation into a body.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A magnetically suspended pump, comprising:

a disk shaped impeller;

a passive bearing for passively controlling two radial axes of said impeller;

an active bearing including three position sensors and three electromagnets circumferentially provided at equal distances opposite to said impeller for actively controlling two axes around the center of gravity of said impeller and the axial direction of said impeller; and control means for executing a prescribed operation based on the output signals of said three position sensors to generate a feedback signal for each electromagnet, thereby controlling a corresponding electromagnet, wherein said control means performs operations based on the following expressions as said prescribed operation:

Z=(S1+S2+S3)/3
S1'=Z+(Z-S3)=(2S1+2S2-S3)/3
S2'=(-S1+2S2-2S3)/3
S3'=(2S1-S2+2S3)/3, wherein the component of said axial direction is Z, the outputs of said three position sensors are S1, S2 and S3, and the impeller displacements of said three electromagnets are S1', S2' and S3'.

2. The magnetically suspended pump as recited in claim 1, wherein said passive bearing includes a first permanent magnet provided on one side of said impeller, and a rotor provided opposite to the other side of said impeller and having a second permanent magnet opposing said first magnet.

3. The magnetically suspended pump as recited in claim 2, further comprising a motor for rotating said impeller by driving said rotor to rotate.

4. The magnetically suspended pump as recited in claim 1, comprising a soft iron member provided opposite to said electromagnets.

\* \* \* \* \*